United States Patent
Xu et al.

(10) Patent No.: US 8,644,652 B2
(45) Date of Patent: Feb. 4, 2014

(54) SLOTTED OPTICAL FIBERS AND METHODS AND APPARATUSES FOR THE SAME

(75) Inventors: Fei Xu, Jiangsu (CN); Junlong Kou, Jiangsu (CN); Yanqing Lu, Jiangsu (CN); Wei Hu, Jiangsu (CN)

(73) Assignee: Empire Technology Development LLC, Wilmington, DE (US)

( * ) Notice: Subject to any disclaimer, the term of this patent is extended or adjusted under 35 U.S.C. 154(b) by 125 days.

(21) Appl. No.: 13/510,925

(22) PCT Filed: Jun. 29, 2011

(86) PCT No.: PCT/CN2011/076558
§ 371 (c)(1),
(2), (4) Date: May 18, 2012

(87) PCT Pub. No.: WO2013/000131
PCT Pub. Date: Jan. 3, 2013

(65) Prior Publication Data
US 2013/0114923 A1    May 9, 2013

(51) Int. Cl.
*G02B 6/10* (2006.01)
*G02B 6/34* (2006.01)

(52) U.S. Cl.
USPC ............................ 385/12; 385/37; 385/123

(58) Field of Classification Search
USPC .................. 385/12, 37, 30, 39, 123, 129
See application file for complete search history.

(56) References Cited

U.S. PATENT DOCUMENTS

| | | |
|---|---|---|
| 5,077,087 A | 12/1991 | Byer et al. |
| 6,134,356 A | 10/2000 | Monte |
| 6,485,191 B1 * | 11/2002 | Sato .............................. 385/73 |
| 2011/0043818 A1 | 2/2011 | Sumetsky |
| 2011/0075963 A1 | 3/2011 | Choi et al. |

FOREIGN PATENT DOCUMENTS

CN    102043191 A    5/2011

OTHER PUBLICATIONS

G. Brambilla, F. Koizumi, X. Feng, and D. J. Richardson, "Compound-glass optical nanowires", Electronics Letters, vol. 41, Issue 7, 400-402 (Mar. 31, 2005).

G. Brambilla, F. Xu, P. Horak, Y. Jung, F. Koizumi, N.P. Sessions, E. Koukharenko, X. Feng, G. S. Murugan, J. S. Wilkinson, and D. J. Richardson, "Optical fiber nanowires and microwaves: fabrication and applications", Advances in Optics and Phonics, vol. 1, Issue 1, 107-161 (2009).

J. Noda, K. Okamoto, and Y. Sasaki, "Polarization-maintaining fibers and their applications", Journal of Lightwave Technology, vol. LT-4, 1071-1089 (Aug. 1986).

(Continued)

*Primary Examiner* — Uyen Chau N Le
*Assistant Examiner* — Michael Mooney
(74) *Attorney, Agent, or Firm* — Knobbe, Martens, Olson & Bear LLP

(57) ABSTRACT

The present application relates to optical fibers having at least one slot. The optical fiber may be used, for example, in various sensing application. In some embodiments, a cross-section of the optical fiber perpendicular to the longitudinal axis has a largest dimension less than or equal to about 4 μm, and the slot has a width of about 5 nm to about 500 nm and a depth of at least about 10 nm. Also disclosed herein are methods of using the optical fibers and apparatuses including the optical fibers.

21 Claims, 6 Drawing Sheets

(56) References Cited

OTHER PUBLICATIONS

L. Tong, R. R. Gattass, J. B. Ashcom, S. He, J. Lou, M. Shen, I. Maxwell, and E. Mazur, "Subwavelength-diameter silica wires for low-loss optical wave guiding", Nature 426, 816-819 (Dec. 18, 2003).
Almeida, V. R., et al., "Guiding and confining light in void nanostructure," Optics Letters 29, 1209-1211, [Jun. 2004].
Brambilla, G., "Optical fibre nanowires and microwires: a review," Journal of Optics 12, [Mar. 2010].
Brambilla, G., et al., "Ultra-low-loss optical fiber nanotapers," Optics Express 12, 2258-2263, [May 2004].
Delgado-Pinar, M., et al., "Waveguiding properties of a photonic crystal fiber with a solid core surrounded by four large air holes," Opt. Express 17, 6931-6938, [Apr. 2009].
Ecke, W., et al, "Fiber Bragg grating optochemical sensor basing on evanescent-field interaction with surface plasmon waves," *Proc. of SPIE*, vol. 7293, 72930A-1 to 72930A-8, [Mar. 2009].
Frazao, O., "Fiber-Optic Interferometric Torsion Sensor Based on a Two-LP-Mode Operation in Birefringent Fiber," Photonics Technology Letters, IEEE 21, 1277-1279, [Sep. 2009].
Hosaka, T., "Low-Loss Single Polarization Fibers with Asymmetrical Strain Birefringence," Electron. Lett. 17, 530-531, [Jul. 1981].
Jung, Y. M., et al., "Highly birefringent silica microfiber," Optics Letters 35, 378-380, [Jan. 2010].
Jung, Y. M., et al., "Polarization-maintaining optical microfiber," Optics Letters 35, 2034-2036, [Jun. 2010].
Kou, J.-I., et al., "Microfiber-probe-based ultrasmall interferometric sensor," Opt. Lett. 35, 2308-2310, [Jun. 2010].
Kou, J.-I., et al., "Miniaturized fiber taper reflective interferometer for high temperature measurement," Opt. Express 18, 14245-14250, [Jun. 2010].
Varnham, M. P., et al., "Single-Polarization Operation of Highly Birefringent Bow-Tie Optical Fibers," Electron. Lett. 19, 246-247, [Mar. 1983].
White, et al, "Refractometric Sensors for Lab-on-a-Chip Based on Optical Ring Resonators," IEEE Sensors Journal, vol. 7, No. 1, pp. 28-35, Jan. 2007.
Xuan, H., et al., "Highly birefringent optical microfibers," Opt. Express 18, 3828-3839, [Feb. 2010].
Yimit, et al., "Thin film composite optical waveguides for sensor applications: a review," *Talanta*, 65 (2005) 1102-1109, [Mar. 2005].
Zhang, L., et al., "Photonic crystal fibers with squeezed hexagonal lattice," Opt. Express 12, 2371-2376, [May 2004].
International Search Report received Apr. 5, 2012 in PCT/CN2011/076558.

* cited by examiner

SLOTTED OPTICAL FIBERS AND METHODS AND APPARATUSES FOR THE SAME

CROSS-REFERENCE TO RELATED APPLICATIONS

This application is the U.S. National Phase under 35 U.S.C. §371 of International Application No. PCT/CN2011/076558, filed Jun. 29, 2011. The International Application was filed in English. The contents of the International Application are hereby incorporated by reference in their entirety.

BACKGROUND

Optical fibers may be used for sensing changes in an ambient medium. Optical sensors have been used to measure or detect changes in various parameters such as temperature, pressure, sound, refractive index and the like. Optical sensors can also be used to detect the presence of an analyte within a medium. In many cases, these characteristics are detected by monitoring the transmission (or reflection) spectrum of light as it propagates along an optical waveguide disposed within the ambient. Some optical fibers function as evanescent sensors based on the detection of changes in light propagating through an optical waveguide due to the optical mode that evanescently penetrates into the surrounding ambient medium.

SUMMARY

The foregoing summary is illustrative only and is not intended to be in any way limiting. In addition to the illustrative aspects, embodiments, and features described above, further aspects, embodiments, and features will become apparent by reference to the drawings and the following detailed description.

Some embodiments disclosed herein include an optical fiber including: a first portion, a second portion, and at least one slot disposed between the first portion and the second portion, the slot extending along a longitudinal axis of the optical fiber. In some embodiments, the cross-section of the optical fiber perpendicular to the longitudinal axis has a largest dimension less than or equal to about 4 µm. In some embodiments, the slot has a width of about 5 nm to about 500 nm and a depth of at least about 10 nm.

In some embodiments, the optical fiber includes a first surface extending along the longitudinal axis of the optical fiber and adjacent to the first portion of the optical fiber. In some embodiments, the optical fiber includes a second surface extending along the longitudinal axis of the optical fiber and adjacent to the second portion of the optical fiber. In some embodiments, the first surface is approximately planar. In some embodiments, the second surface is approximately planar.

In some embodiments, the first surface extends from an outer surface of the optical fiber to an inner region of the optical fiber along an axis perpendicular to the longitudinal axis. In some embodiments, the second surface extends from an outer surface of the optical fiber to an inner region of the optical fiber along an axis perpendicular to the longitudinal axis. In some embodiments, the first surface and the second surface are generally parallel.

In some embodiments, the slot includes a third surface extending between the first surface and the second surface. In some embodiments, the third surface is generally planar.

In some embodiments, the first surface and the third surface form a first angle of about 30° to about 150°. In some embodiments, the first angle is about 90°. In some embodiments, the second surface and third surface form a second angle of about 30° to about 150°. In some embodiments, the second angle is about 90°.

In some embodiments, the first surface and the second surface meet to form a vertex. In some embodiments, the first surface and a second surface form an angle of about 15° to about 120°. In some embodiments, the vertex is disposed along a plane that bisects the optical fiber. In some embodiments, the vertex is located at about a center axis of the optical fiber.

In some embodiments, a center axis of optical microfiber is at least partially disposed within the slot. In some embodiments, the optical fiber has an approximately mirror image plane along the longitudinal axis of the optical fiber.

In some embodiments, the slot has a length of at least about 50 µm. In some embodiments, a length of the optical fiber is greater than a length of the slot. In some embodiments, the optical fiber has a length of at least about 50 µm.

In some embodiments, the optical fiber includes a third portion and a second slot disposed between the second portion and the third portion. In some embodiments, the second slot has a width of about 5 nm to about 500 nm and a depth of at least about 10 nm. In some embodiments, the width of the slot is about the same as the width of the second slot.

In some embodiments, the width of the slot is different from the width of the second slot. In some embodiments, the depth of the slot is about the same as the depth of the second slot. In some embodiments, the depth of the slot is different from the depth of the second slot.

In some embodiments, the optical fiber includes three or more slots.

In some embodiments, the optical fiber includes a polymer, silicon, silica, or combinations thereof In some embodiments, the optical fiber has an attenuation coefficient at a wavelength of 1550 nm of about 2 dB/km or less.

In some embodiments, the optical fiber includes a plurality of gratings disposed on an outer surface of the optical fiber. In some embodiments, the gratings are spaced at repeating intervals along the longitudinal axis of the optical fiber.

Some embodiments disclosed herein include a method for sensing characteristics of a medium. In some embodiments, the method includes: providing an optical fiber disposed adjacent to a medium, transmitting light through the optical fiber from a first end of the optical fiber to a second end of the optical fiber, and measuring at least one characteristic of the light from the optical fiber. In some embodiments, the optical fiber includes: a first portion, a second portion, and at least one slot disposed between the first portion and the second portion. In some embodiments, the slot extends along a longitudinal axis of the optical fiber. In some embodiments, a cross-section of the optical fiber perpendicular to the longitudinal axis has a largest dimension less than or equal to about 4 µm. In some embodiments, the slot has a width of about 5 nm to about 500 nm. In some embodiments, the slot has a depth of at least about 10 nm.

In some embodiments, the at least one characteristic of the light from the optical fiber is intensity, phase, or polarization. In some embodiments, the method includes correlating the at least one characteristic of the light from the optical fiber with at least one characteristic of the medium. In some embodiments, the method includes correlating a change in at least one characteristic of the light from the optical fiber with a change in at least one characteristic of the medium.

In some embodiments, the at least one characteristic of the medium is temperature, pressure, tension, index of refraction, or concentration of at least one component in the medium.

Some embodiments disclosed herein include a sensing device. In some embodiments, the sensing device includes: a light source, an optical fiber configured to receive at least a portion of the light from the light source at a first end and transmit the light to a second end, a light detector configured to receive at least a portion of the light from the second end of the optical fiber and measure at least one characteristic of the light from the optical fiber. In some embodiments, the optical fiber includes: a first portion, a second portion, and at least one slot disposed between the first portion and the second portion. In some embodiments, the slot extends along a longitudinal axis of the optical fiber. In some embodiments, a cross-section of the optical fiber perpendicular to the longitudinal axis has a largest dimension less than or equal to about 4 μm. In some embodiments, the slot has a width of about 5 nm to about 500 nm. In some embodiments, the slot has a depth of at least about 10 nm.

In some embodiments, the at least one characteristic of the light from the optical fiber is intensity, phase, or polarization.

In some embodiments, the sensing device includes a polarizer configured to polarize the light before transmitting through the optical fiber.

In some embodiments, the sensing device includes a splitter configured to divide the light from the light source into two or more beams, wherein at least one beam is not configured to transmit through the optical fiber.

In some embodiments, the sensing device includes a processor coupled to the light detector and configured to receive signals corresponding to the at least one characteristic of the light from the optical fiber. In some embodiments, the processor is configured to correlate the at least one characteristic of the light from the optical fiber with at least one characteristic of a medium adjacent to the optical fiber. In some embodiments, the processor is coupled to the light source and configured to send and/or receive signals corresponding to at least one characteristic of the light from the light source.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through use of the accompanying drawings.

DETAILED DESCRIPTION

Figure 1A:
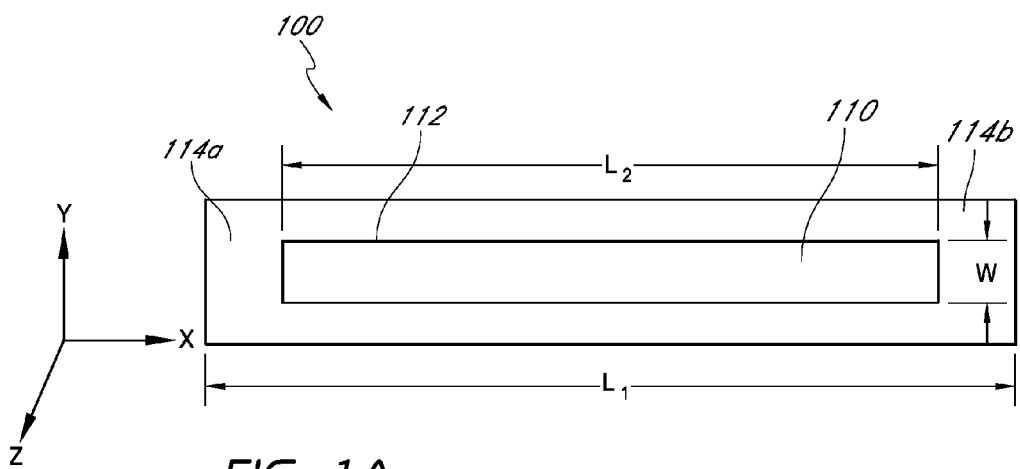
FIGS. 1A-C shows a top, perspective, and cross-section views, respectively, of an illustrative embodiment of an optical fiber that is within the scope of the present application (not to scale).

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

Disclosed herein are optical fibers including at least one slot extending along a longitudinal axis of the optical fiber. The optical fiber may, for example, have a radius less than or equal to about 2 μm. The slot may, for example, have a width of about 5 nm to about 500 nm and a depth of at least about 10 nm. The optical fiber may, in some embodiments, produce a large evanescent field for improved sensing of one or more characteristics of a medium. The optical fiber may, in some embodiments, produce large birefringence for improved sensing of one or more characteristics of a medium.

Slotted Microfibers

Figure 1B:
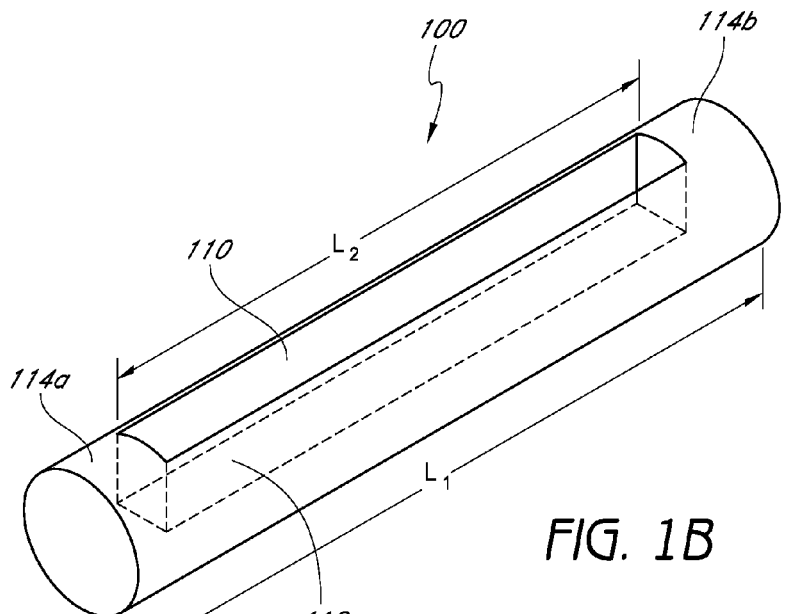

Some embodiments disclosed herein include an optical fiber having one or more slots. FIG. 1A shows a top view of one example of an optical fiber that is within the scope of the present application. Optical fiber 100 includes a slot 110 extending along a longitudinal axis of optical fiber 100 (e.g., along the x-axis as depicted in FIG. 1A). Optical fiber 100 can have length $L_1$ along the longitudinal axis. Slot 110 can have length $L_2$ extending along the longitudinal axis. Slot 110 may also have width W extending perpendicular to the longitudinal axis (e.g., along the y-axis as depicted in FIG. 1A). Slotted portion 112 along the longitudinal axis of optical fiber 100 includes slot 110, while first non-slotted portion 114a and second non-slotted portion 114b of optical fiber 100 do not include slot 110. FIG. 1B shows a perspective view of optical fiber 100 having slot 110.

Figure 1C:
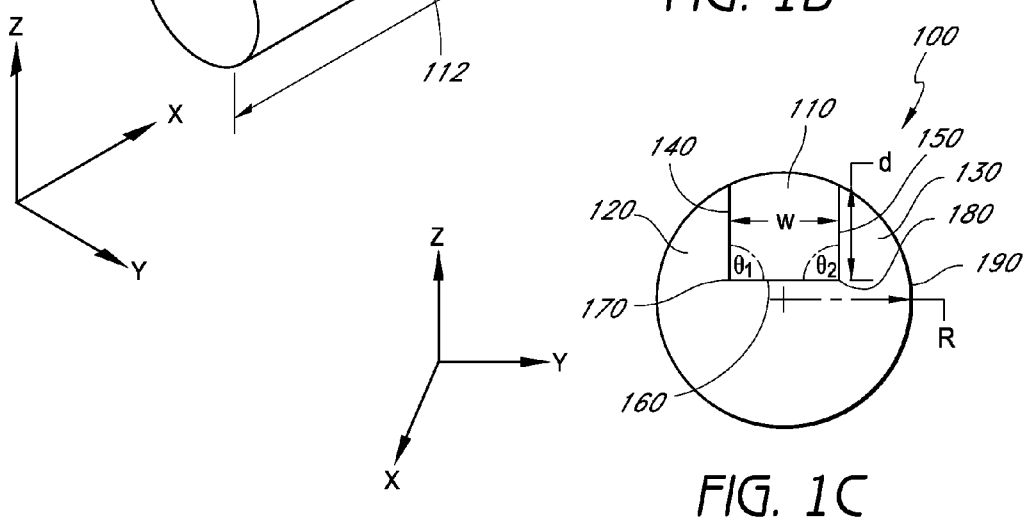

FIG. 1C shows a cross-sectional view at about the midpoint of optical fiber 100 and perpendicular to the longitudinal axis of optical fiber 100. Optical fiber 100 can have a circular cross-section with a radius R. Slot 110 can have depth d extending perpendicular to both the longitudinal axis and width W (e.g., along the z-axis depicted in FIG. 1C). Slot 110 is disposed between first portion 120 and second portion 130 of optical fiber 100. Slot 110 can include first surface 140, second surface 150, and third surface 160, each extending along the longitudinal direction of optical fiber 100. First surface 140 and third surface 160 meet at first vertex 170 to form an angle $\theta_1$, while second surface 150 and third surface 160 meet at first vertex 180 to form an angle $\theta_2$. First surface 140 extends from outer surface 190 of optical fiber 100 to first vertex 170, while second surface 150 extends from outer surface 190 of optical fiber 100 to second vertex 180.

The shape and dimensions for the optical fiber (e.g., optical fiber 100 depicted in FIGS. 1A-C) are not particularly limited, and may be selected, for example, based upon the desired sensor configuration. For example, the length of the optical fiber (e.g., the length $L_1$ of optical fiber 100 depicted in FIGS. 1A-C) can be varied depending upon various factors, such as the desired sensitivity of the sensor. The length of the optical fiber may generally be any length, for example, at least about 50 µm; at least about 75 µm; at least about 100 µm; at least about 250 µm; or at least about 500 µm. The length of the optical fiber may also be, for example, less than or equal to about 1 m; less than or equal to about 10 cm; less than or equal to about 1 cm; less than or equal to about 5 mm; less than or equal to about 1 mm; or less than or equal to about 500 µm. In some embodiments, the optical fiber may have a length of at least about 50 µm. In some embodiments, the optical fiber may have a length from about 50 µm to about 1 m.

As used herein, the "non-slotted cross-section" refers to the cross-section of the optical fiber that is perpendicular to the longitudinal axis and does not include the slot (e.g., as depicted by first non-slotted portion 114a and second non-slotted portion 114b in FIGS. 1A-B). The non-slotted cross-section can have various shapes and is not particularly limited. For example, the non-slotted cross-section may be circular, elliptical, polygonal, and the like. In some embodiments, the cross-section is circular. In some embodiments, the non-slotted cross-section is elliptical. In some embodiments, the non-slotted cross-section is polygonal having three sides or more (e.g., 3, 4, 5, 6, 7, 8, 9, 10, 11, 12, 13, 14, 15, 16, 17, 18, 19, 20, or more sides). The non-slotted cross-section, in some embodiments, can include two-fold, three-fold, four-fold, five-fold, six-fold, or higher rotational symmetry.

A ratio of a largest dimension of the non-slotted cross-section to a smallest dimension of the non-slotted cross-section may be, for example, at least about 1:1; at least about 1.2:1; at least about 1.3:1; at least about 1.5:1; or at least about 2:1. A ratio of a largest dimension of the cross-section to a smallest dimension of the cross-section may also be, for example, less than or equal to about 5:1; less than or equal to about 3:1; less than or equal to about 2:1; less than or equal to about 1.5:1; less than or equal to about 1.3:1; or less than or equal to about 1.1:1. In some embodiments, a ratio of a largest dimension of the cross-section to a smallest dimension of the cross-section is from about 1:1 to about 5:1. In some embodiments, a ratio of a largest dimension of the cross-section to a smallest dimension of the cross-section is about 1:1.

The largest dimension for the non-slotted cross-section of the optical fiber may also vary. The largest dimension for the non-slotted cross-section of the optical fiber can be, for example, less than or equal to about 4 µm; less than or equal to about 3.5 µm; less than or equal to about 3 µm; less than or equal to about 2.5 µm; less than or equal to about 2 µm; less than or equal to about 1.5 µm; or less than or equal to about 1 µm. The largest dimension for the non-slotted cross-section of the optical fiber can be, for example, at least about 50 nm; at least about 100 nm; at least about 250 nm; at least about 500 nm; at least about 800 nm; at least about 1 µm; at least about 1.5 µm; or at least about 2 µm. In some embodiments, the largest dimension for the non-slotted cross-section of the optical fiber is less than or equal to about 4 µm. In some embodiments, the largest dimension for the non-slotted cross-section of the optical fiber is from about 50 nm to about 4 µm.

The non-slotted cross-section may, in some embodiments, be about the same along the longitudinal axis in portions without the slot. For example, the non-slotted cross-section may be a circle having a constant radius (e.g., a radius of about 1 µm) along the length of the optical fiber. In some embodiments, the largest dimension (or diameter) of the non-slotted cross-section can have less than about 25% deviation (or less than about 10% deviation) from an average of the largest dimension for the non-slotted cross-sections along the optical fiber. In some embodiments, the area of the non-slotted cross-section can be about the same along the non-slotted cross-sections of the optical fiber. For example, the area of the non-slotted cross-section can have less than about 25% deviation (or less than about 10% deviation) from an average area of the non-slotted cross-sections along the optical fiber.

As used herein, the "slotted cross-section" refers to the cross-section of the optical fiber that is perpendicular to the longitudinal axis and includes the slot (e.g., as depicted by slotted portion 112 in FIGS. 1A-B). The shape of the slotted cross-section is also not particular limited. In some embodiments, the shape of the slotted cross-section corresponds to the shape of the non-slotted cross-section. That is, the differences in shape between the slotted and non-slotted cross-sections are due to the slot. As an example, the non-slotted cross-section can have a circular cross-section with a diameter of about 2 µm and the slotted cross-section can be a circle with a 2 µm diameter and slot formed within the circle. In some embodiments, the slotted cross-section may have a slot formed within a circle, ellipse, polygon, and the like. In some embodiments, the slotted cross-section has a slot formed into a circle. In some embodiments, the cross-section has a slot formed into an ellipse. In some embodiments, the slotted cross-section has a slot formed into polygon having three sides or more (e.g., 3, 4, 5, 6, 7, 8, 9, 10, 11, 12, 13, 14, 15, 16, 17, 18, 19, or 20 sides). The slotted cross-section, in some embodiments, can include at two-fold, three-fold, four-fold, five-fold, six-fold, or higher rotational symmetry.

The largest dimension for the slotted cross-section of the optical fiber may also vary. The largest dimension for the slotted cross-section of the optical fiber can be, for example, less than or equal to about 4 µm; less than or equal to about 3.5 µm; less than or equal to about 3 µm; less than or equal to about 2.5 µm; less than or equal to about 2 µm; less than or equal to about 1.5 µm; or less than or equal to about 1 µm. The largest dimension for the slotted cross-section of the optical fiber can be, for example, at least about 50 nm; at least about 100 nm; at least about 250 nm; at least about 500 nm; at least about 800 nm; at least about 1 µm; at least about 1.5 µm; or at least about 2 µm. In some embodiments, the largest dimension for the slotted cross-section of the optical fiber is less than or equal to about 4 µm. In some embodiments, the largest dimension for the slotted cross-section of the optical fiber is from about 50 nm to about 4 µm. In some embodiments, the largest dimension for the slotted cross-section is about the same as the largest dimension for the non-slotted cross-section.

As used herein, the "radius" of the optical fiber is one half of the largest dimension for the cross-section of the optical fiber unless expressly defined otherwise. As an example, the cross-section may be a circle having a largest dimension of about 3 µm, and therefore has a radius of about 1.5 µm.

The shape of the slot disposed within the optical fiber is not particularly limited and can vary depending upon the desired properties for the optical fiber. In some embodiments, the shape and dimensions are effective for the slot to function as a waveguide for light. The shape of the slot may, for example, be defined by one or more surfaces (e.g., one, two, three, four, five, six, seven, eight, or more surfaces), each extending along the longitudinal axis of the optical fiber.

The one or more surfaces can be planar surfaces, curved surfaces, or a combination thereof. In some embodiments, the slot is bounded by two or more planar surfaces. In some embodiments, the slot includes a first surface extending from an outer surface of the optical fiber to an inner region of the optical fiber. In some embodiments, the slot includes a second surface extending from an outer surface of the optical fiber to an inner region of the optical fiber.

In some embodiments, the slot includes at least two surfaces. In some embodiments, the first surface and second surface meet at a vertex. In some embodiments, the first and second surface form an angle from about 12° to about 120°. Non-limiting examples for the angle between the first and second surface include about 12°, about 30°, about 60°, about 90°, about 120°, or a range between any two of these values.

Figure 2:
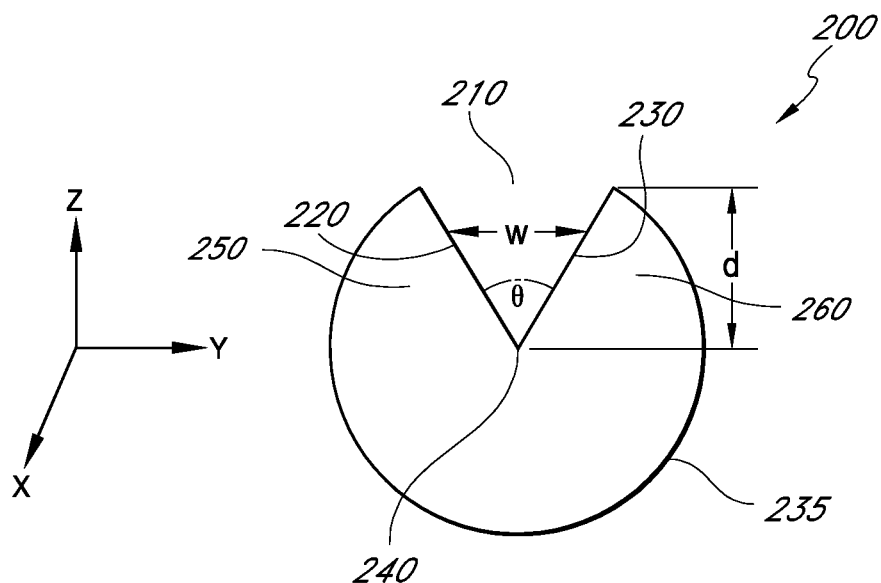
FIG. 2 is a cross-section of an illustrative embodiment of an optical fiber having a slot that includes two surfaces (not to scale).

FIG. 2 is one example of an optical fiber having a slot that includes two surfaces. Optical fiber 200 has slot 210 including first surface 220 and second surface 230 which meet at vertex 240 to form an angle θ. First surface 220 and second surface 230 both extend along the longitudinal axis of optical fiber 200 (e.g., along the x-axis as depicted in FIG. 2). First surface 220 extends from outer surface 235 of optical fiber 200 to vertex 240, while second surface 230 extends from outer surface 235 of optical fiber 200 to vertex 240. Slot 210 is also disposed between first portion 250 and second portion 260. Slot 210 can have depth d extending perpendicular to both the longitudinal axis and width W (e.g., along the z-axis depicted in FIG. 2). In some embodiments, the angle θ can be from about 12° to about 120°. Non-limiting examples for the angle θ include about 12°, about 30°, about 60°, about 90°, about 120°, or a range between any two of these values.

In some embodiments, the slot includes a third surface that forms a vertex with the first surface. The first and third surfaces may, for example, form an angle of about 30° to about 150°. Other non-limiting examples for the angle between the first and third surfaces includes about 30°, about 60°, about 90°, about 120°, about 150°, or a range between any two of these values. In some embodiments, the third surface forms a vertex with the second surface. The second and third surfaces may, for example, form an angle of about 30° to about 150°. Other non-limiting examples for the angle between the second and third surfaces includes about 30°, about 60°, about 90°, about 120°, about 150°, or a range between any two of these values. In some embodiments, the angle between the first and third surfaces is about the same as the angle between the second and third surfaces. In some embodiments, the first surface and the second surface are generally parallel.

Returning to FIGS. 1A-C, optical fiber 100 is an example of an optical fiber having three surfaces. Slot 110 includes three surfaces: first surface 140, second surface 150, and third surface 160. First surface 140 and third surface 160 meet at first vertex 170 to form an angle $\theta_1$, while second surface 150 and third surface 160 meet at first vertex 180 to form an angle $\theta_2$. In some embodiments, the angle $\theta_1$ can be from about 30° to about 150°. Non-limiting examples for the angle $\theta_1$ includes about 30°, about 60°, about 90°, about 120°, about 150°, or a range between any two of these values. In some embodiments, the angle $\theta_2$ can be from about 30° to about 150°. Non-limiting examples for the angle $\theta_2$ includes about 30°, about 60°, about 90°, about 120°, about 150°, or a range between any two of these values. In some embodiments, $\theta_1$ and $\theta_2$ are about the same or are the same. For example, $\theta_1$ and $\theta_2$ may both be about 90°.

In some embodiments, the slot is bounded by one or more curved surfaces. The one or more curved surfaces may, in some embodiments, extend from an outer surface of the optical fiber to an inner region of the optical fiber. In some embodiments, the slot includes one curved surface that extends from a first location on the outer surface of the optical fiber to a second location on the outer surface of the optical fiber to form the slot.

Figure 3:
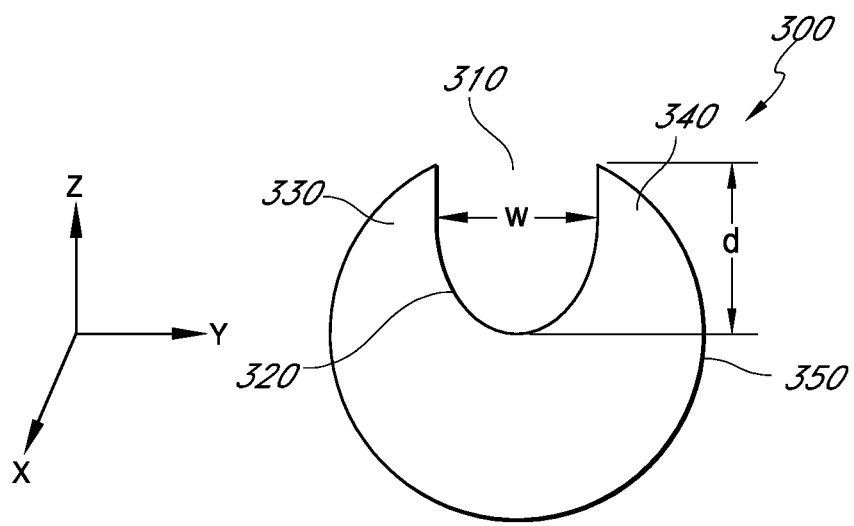
FIG. 3 is a cross-section of an illustrative embodiment of an optical fiber having a slot that includes a curved surface (not to scale).

FIG. 3 is one example of an optical fiber having a slot that includes a curved surface. Optical fiber 300 has slot 310 which includes 'U'-shaped surface 320 that bounds slot 310 and extends along the longitudinal axis of optical fiber 300 (e.g., along the x-axis as depicted in FIG. 3). Slot 310 is also disposed between first portion 330 and second portion 340. 'U'-shaped surface 320 also extends between two locations on outer surface 350 of optical fiber 300. Slot 310 can have depth "d" extending perpendicular to both the longitudinal axis and width "W" (e.g., along the z-axis depicted in FIG. 3). Although FIG. 3 shows one example of a slot having a curved surface, numerous other curved surfaces are possible and within the scope of the present application.

The depth of the slot can be varied (e.g., depth d as depicted in FIG. 1C) to alter the properties of the optical fiber. Without being bound to any particular theory, it is believed that increasing the depth can enhance optical birefringence and evanescent fields. The depth can be, for example, at least about 10 nm; at least about 50 nm; at least about 100 nm; at least about 250 nm; at least about 500 nm; at least about 750 nm; at least about 1 μm; at least about 1.5 μm; at least about 2 μm; at least about 2.5 μm; at least about 3 μm; or at least about 3 μm. The depth can be, for example, less than or equal to about 4 μm; less than or equal to about 3.5 μm; less than or equal to about 3 μm; less than or equal to about 2.5 μm; less than or equal to about 2 μm; less than or equal to about 1.5 μm; or less than or equal to about 1 μm. In some embodiments, the depth is from about 10 nm to about 4 nm.

The depth may also be configured relative to the largest dimension for the cross-section of the optical fiber (or diameter). As an example, an optical fiber may have a diameter of 2 μm and a slot with a depth of 1 μm. The depth would therefore be 50% of the largest dimension for the cross-section of the optical fiber. The depth can be, for example, at least about 1% of the largest dimension; at least about 10% of the largest dimension; at least about 20% of the largest dimension; at least about 30% of the largest dimension; at least about 40% of the largest dimension; at least about 50% of the largest dimension; at least about 60% of the largest dimension; and at least about 70% of the largest dimension. The depth can also be, for example, less than or equal to about 99% of the largest dimension; less than or equal to about 90% of the largest dimension; less than or equal to about 80% of the largest dimension; less than or equal to about 70% of the largest dimension; less than or equal to about 60% of the largest dimension; or less than or equal to about 50% of the largest dimension. In some embodiments, the depth is from about 1% to about 99% of the largest dimension for the cross-section of the optical fiber. In some embodiments, the depth is less than the largest dimension for the cross-section of the optical fiber.

The width of the slot can also be varied (e.g., width W as depicted in FIG. 1C) to alter the properties of the optical fiber. Without being bound to any particular theory, it is believed that adjusting the width can enhance optical birefringence and evanescent fields. The width can be, for example, at least about 5 nm; at least about 10 nm; at least about 25 nm; at least about 50 nm; at least about 100 nm; at least about 200 nm; at least about 250 nm; at least about 300 nm; or at least about 400 nm. The width can be, for example, less than or equal to about 500 nm; less than or equal to about 450 nm; less than or equal to about 400 nm; less than or equal to about 300 nm; less than or equal to about 250 nm; less than or equal to about 200 nm or less than or equal to about 100 nm. In some embodiments, the width is from about 5 nm to about 500 nm.

The width may also be configured relative to the largest dimension for the cross-section of the optical fiber (or diameter). As an example, an optical fiber may have a diameter of 2 μm and a slot with a width of 500 nm. The width would be 25% of the largest dimension for the cross-section of the optical fiber. The width can be, for example, at least about 0.1% of the largest dimension; at least about 0.5% of the largest dimension; at least about 1% of the largest dimension; at least about 5% of the largest dimension; at least about 10% of the largest dimension; at least about 15% of the largest dimension; at least about 20% of the largest dimension; or at least about 25% of the largest dimension. The width can be, for example, less than or equal to about 99% of the largest dimension; less than or equal to about 90% of the largest dimension; less than or equal to about 70% of the largest dimension; less than or equal to about 50% of the largest dimension; less than or equal to about 40% of the largest dimension; or less than or equal to about 30% of the largest dimension. In some embodiments, the width is from about 1% to about 99% of the largest dimension for the cross-section of the optical fiber. In some embodiments, the width is less than the largest dimension for the cross-section of the optical fiber.

The width may also be configured relative to the depth of the slot. As an example, the slot may have a width of 100 nm and a depth of 500 nm; therefore, the width is 20% of the depth. The width can be, for example, at least about 1% of the depth; at least about 10% of the depth; at least about 20% of the depth; at least about 30% of the depth; at least about 40% of the depth; at least about 50% of the depth; at least about 60% of the depth; and at least about 70% of the depth. The width can also be, for example, less than or equal to about 99% of the depth; less than or equal to about 90% of the depth; less than or equal to about 80% of the depth; less than or equal to about 70% of the depth; less than or equal to about 60% of the depth; or less than or equal to about 50% of the depth. In some embodiments, the width is from about 1% to about 99% of the depth of the slot. In some embodiments, the width is less than the depth of the slot.

The length of the slot is not particularly limited and can be any value up to the length of the optical fiber. The length of the slot can be, for example, at least about 50 μm; at least about 100 μm; at least about 150 μm; at least about 200 μm; at least about 250 at least about 300 μm; or at least about 1 mm. The length of the slot can be, for example, less than or equal to about 1 m; less than or equal to about 50 cm; less than or equal to about 10 cm; less than or equal to about 1 cm; less than or equal to about 5 mm; less than or equal to about 1 mm; or 500 μm. In some embodiments, the length of the slot is about 50 μm to about 1 m. In some embodiments, the length of the slot is less than the length of the optical fiber.

The shape and dimensions of the slot may, in some embodiments, be about the same along the length of the slot. For example, the slot may be configured as depicted in FIGS. 1A-C where the width, depth, $\theta_1$, and $\theta_2$ are all constant along the length of the slot (e.g., along length $L_2$ for optical fiber 100 depicted in FIGS. 1A-B). In some embodiments, the cross-sectional area of the slot perpendicular to the longitudinal axis of the optical fiber can be about the same along the length of the slot. For example, the cross-sectional area of the slot perpendicular to the longitudinal axis of the optical fiber can have less than about 25% deviation (or less than about 10% deviation) from an average area cross-sectional area of the slot along its length. In some embodiments, the area of the slotted cross-section of the optical fiber can be about the same along the length of the slot. For example, the area of the slotted cross-section can have less than about 25% deviation (or less than about 10% deviation) from an average area of the slotted cross-section along the length of the slot.

The relative location of the slot in the optical fiber is not very limited. In some embodiments, a portion of the slot is located at about the mid-point along the length of the optical fiber (e.g., a portion of slot 110 is located at the mid-point along the length of slot 100 as depicted in FIGS. 1A-B). The slot may, in some embodiments, be centered within the cross-section of the optical fiber. Accordingly, the slotted cross-section may, for example, be configured such that at least one plane extending along the longitudinal axis and through a center of the slotted cross-section bisects the slot into equal portions. In some embodiments, the slotted cross-section includes at least one mirror image plane extending along the longitudinal axis of the optical fiber. In some embodiments, the slot includes the center of the slotted cross-section. For example, both the depth d and width W can be greater than the radius R depicted in FIG. 1C so that the center of the optical fiber cross-section is within the slot.

Figure 4:
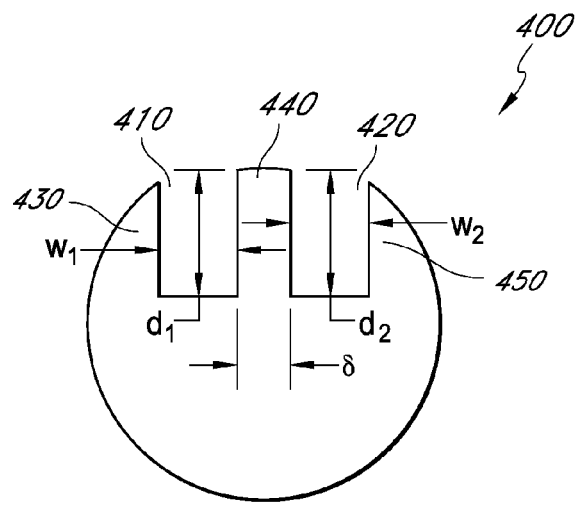
FIG. 4 is a cross-section of an illustrative embodiment of an optical fiber having two slots (not to scale).

Some embodiments of the optical fiber can include at two or more slots (e.g., two, three, four, or more slots) within the microfiber. The two or more slots may have about the same shape, the same shape, or different shapes. In some embodiments, the two or more slots have about the same dimensions. In some embodiments, the two or more slots have different dimensions. FIG. 4 is a cross-section of one example of an optical fiber having two slots. Optical fiber 400 includes first slot 410 having a depth $d_1$ and a width $W_1$. Optical fiber 400 also includes second slot 420 having a depth $d_2$ and a width $W_2$. First slot 410 is disposed between first portion 430 and second portion 440 of the optical fiber. Second slot 420 is disposed between second portion 440 and third portion 450 of the optical fiber. First slot 410 and second slot 420 can be a distance δ apart. The distance δ can be, for example, at least about 10 nm; at least about 25 nm; at least about 50 nm; at least about 100 nm; at least about 250 nm; at least about 500 nm; or at least about 1 μm.

Figure 5:
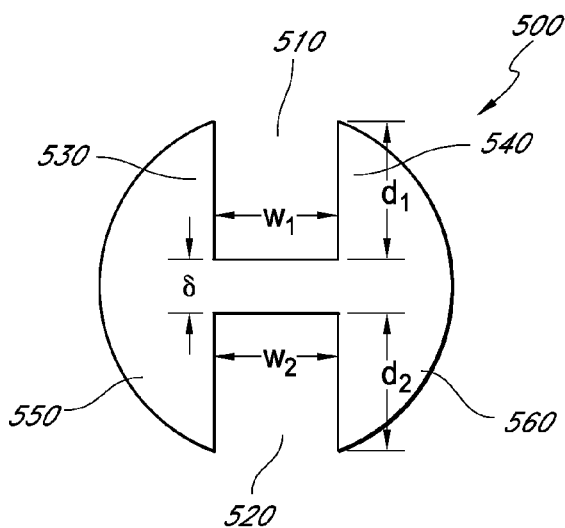
FIG. 5 is a cross-section of an illustrative embodiment of an optical fiber having two slots on opposing sides (not to scale).

In some embodiments, the optical fiber can include two slots on opposing sides of the optical fiber. FIG. 5 is a cross-section of one example of an optical fiber having two slots on opposing sides. Optical fiber 500 includes first slot 510 having a depth $d_1$ and a width $W_1$. Optical fiber 500 also include second slot 520 having a depth $d_2$ and a width $W_2$. First slot 510 is disposed between first portion 530 and second portion 540 of optical fiber 500. Second slot 520 is disposed between third portion 550 and fourth portion 560 of optical fiber 500. First slot 410 and second slot 420 can be a distance δ apart. The distance δ can be, for example, at least about 10 nm; at least about 25 nm; at least about 50 nm; at least about 100 nm; at least about 250 nm; at least about 500 nm; or at least about 1 μm. The dimensions and location of first slot 510 and second slot 520 may, in some embodiments, be configured such that the slotted cross-section has two-fold rotational symmetry.

Figure 6:
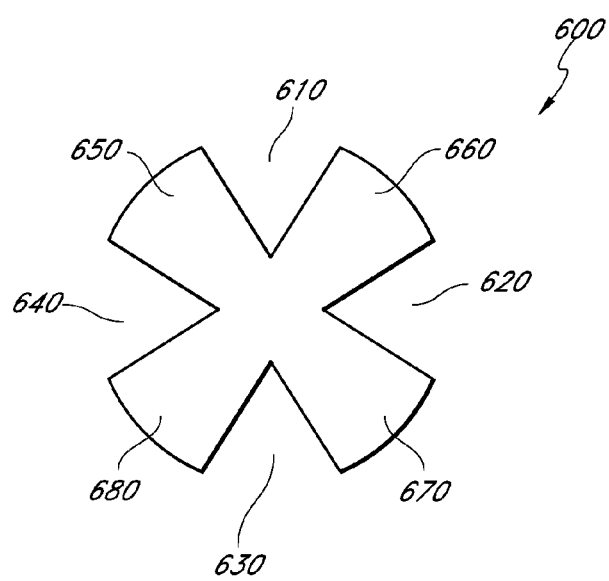
FIG. 6 is a cross-section of an illustrative embodiment of an optical fiber having four slots and four-fold rotational symmetry (not to scale).

Various other configurations can be used having two-fold, three-fold, four-fold, five-fold, six-fold, or higher rotational symmetry. FIG. 6 is a cross-section of one example of an optical fiber having four slots and four-fold rotational symmetry. Optical fiber 600 includes first slot 610, second slot 620, third slot 630, and fourth slot 640. First slot 610 is disposed between first portion 650 and second portion 660 of the optical fiber. Second slot 620 is disposed between second portion 660 and third portion 670 of the optical fiber. Third slot 620 is disposed between third portion 670 and fourth portion 680 of the optical fiber. Fourth slot 620 is disposed between fourth portion 670 and first portion 650 of the optical fiber. Numerous other configurations having rotational symmetry can be used that are readily apparent to the skilled artisan guided by the teachings of the present application.

In some embodiments, the slotted cross-section of the optical fiber has two-fold rotational symmetry or does not include rotational symmetry. In some embodiments, the slotted cross-section of the optical fiber does not include rotational symmetry. By providing a slotted cross-section without three-fold or higher rotational symmetry, the slotted optical fiber may exhibit increased birefringence properties. As discussed above, the birefringence can be used in various sensing application to detect changes in one or more characteristics of a medium.

The optical fiber can be prepared from conventional materials that are commonly used for optical fibers, and particularly for optical fibers in sensing applications. The materials can be transparent materials. The transparent materials, in some embodiments, can be selected and processed so that the optical fiber is transparent to light. The transparent materials can include, for example, glass (e.g., silica), silicon, polymers, and the like. In some embodiments, the optical fiber has an attenuation coefficient at a wavelength of about 1550 nm of about 2 dB/km or less. In some embodiments, the optical fiber has an attenuation coefficient at a wavelength of about 1550 nm of about 1 dB/km or less. In some embodiments, the optical fiber has an attenuation coefficient at a wavelength of about 1550 nm of about 0.5 dB/km or less.

In some embodiments, the optical fiber can include a tapered optical coupler on one or both ends of the optical fiber to receive or transmit light through the ends of the optical fiber.

In some embodiments, the optical fiber can also include fiber Bragg gratings on the outer surface. The fiber Bragg gratings can be used, for example, to detect changes in temperature or strain. Without being bound to any particular theory, it is believed changes in temperature or strain can affect the spacing of the gratings and birefringence of the optical fiber, which in turn may affect the properties of the light that is transmitted through or reflected from the optical fiber (e.g., polarity and wavelength of light transmitted). The fiber Bragg gratings can include two or more gratings (e.g., 2, 3, 4, 5, 6, 7, 8, 9, 10 or more gratings) disposed at repeating intervals. The repeating intervals may be about the same length as the wavelength of light that is transmitted through the optical fiber. For example, the repeating intervals can be about 400 nm to about 2000 nm. Non-limiting examples for the repeating interval include about 400 nm, about 500 nm, about 600 nm, about 700 nm, about 800 nm, about 900 nm, about 1000 nm, about 1100 nm, about 1200 nm, about 1300 nm, about 1400 nm, about 1500 nm, about 1600 nm, about 1700 nm, about 1800 nm, about 1900 nm, about 2000 nm, or a range between any two of these values. The gratings can be prepared using standard methods, such as by inscribing the gratings using ultraviolet light.

In some embodiments, the optical fiber can also include fiber Bragg gratings on the outer surface. The fiber Bragg gratings can be used, for example, to detect changes in temperature or strain. Without being bound to any particular theory, it is believed changes in temperature or strain can affect the spacing of the gratings and birefringence of the optical fiber, which in turn may affect the properties of the light that is transmitted through or reflected from the optical fiber (e.g., polarity and wavelength of light transmitted). The fiber Bragg gratings can include two or more gratings (e.g., 2, 3, 4, 5, 6, 7, 8, 9, 10 or more gratings) disposed at repeating intervals. The repeating intervals may be about the same length as the wavelength of light that is transmitted through the optical fiber. For example, the repeating intervals can be about 400 nm to about 2000 nm. Non-limiting examples for the repeating interval include about 400 nm, about 500 nm, about 600 nm, about 700 nm, about 800 nm, about 900 nm, about 1000 nm, about 1100 nm, about 1200 nm, about 1300 nm, about 1400 nm, about 1500 nm, about 1600 nm, about 1700 nm, about 1800 nm, about 1900 nm, about 2000 nm, or a range between any two of these values. The gratings can be prepared using standard methods, such as by inscribing the gratings using ultraviolet light.

In some embodiments, the optical fiber can include receptors or binding sites on the outer surface of the optical fiber. The receptors or binding sites may bind to an analyte in the ambient medium, which in turn alters the optical properties at the outer surface of the optical fiber. The light spectrum transmitted through the optical fiber may be modified by this change (e.g., the intensity of certain wavelengths transmitted) and correlated with the presence (or concentration) of an analyte in the ambient. As one example, the optical fiber may include an antibody with an affinity for one or more proteins. Changes to the spectrum of light transmitted through the optical fiber may be correlated with the concentration of one or more proteins. Numerous receptors and binding sites are well-known in the art and can be readily used with the optical fibers of the present application.

The optical fiber may be prepared using conventional techniques known to the skilled artisan. The optical fiber may be obtained, for example, by tapering a standard single mode fiber with heat-and-drawing techniques. One example of this technique is disclosed in Brambill, G. et al. "Ultra-low-loss optical fiber nanotapes," *Optics Express* vol. 12, pp. 2258-2263 (2004). The slot can then be formed into the optical fiber by micromachining techniques, such as focused ion beam milling and deep-UV lithography. Kou J., et al. "Microfiber-probe-based ultrasmall interferometric sensor," *Optics Letters* vol. vol. 35, pp. 2308-2310 (2010) and Kou J., et al. "Miniaturized fiber taper interferometer for high temperature measurement," *Optics Express* vol. 18, pp. 14245-14250 (2010) are some examples of publications disclosing processes that may be used to form the one or more slots within the microfiber. Various other methods may be used to prepare the slotted optical fibers and the present application is not limited to any particular method.

Methods of Using Slotted Optical Fibers

Some embodiments disclosed herein include methods of using slotted optical fibers. The methods can use any of the slotted optical fibers disclosed in the present application. For example, any of the slotted optical fibers depicted in FIGS. 1-6 may be used. The slotted optical fiber may be disposed adjacent to or contacting a medium for sensing one or more characteristics of the medium. For example, the method can be used to detect one or more characteristic of a medium selected from temperature, pressure, tension, index of refraction, or concentration of at least one component in the medium. The medium is not particularly limited and may be, for example, a fluid, a gas, a liquid, a solid, an aqueous solution, an organic solution, air, and the like.

In some embodiments, the medium can be a resonator, such as an annulus or disc. The optical fiber may, for example, be coiled two or more times around the resonator. The resonator may exhibit changes in the index of refraction when contacting different materials. U.S. Patent Publication No. 2011/0075963 discloses some examples of resonators that may be used with the optical fibers. In some embodiments, the resonator includes one or more channels or reservoirs for receiving a sample medium. Changes to one or more characteristics of light transmitted through the optical fiber may be measured or detected due to the sample medium provided in the channel(s) or reservoir(s).

In some embodiments, the method can include transmitting light through the optical fiber from a first end of the optical fiber to a second end of the optical, and measuring at least one characteristic of the light from the optical fiber. The characteristic of the light can be, for example, the intensity, phase, or polarization. These characteristics can be measured at one or more wavelengths. For example, the intensity at 850 nm can be measured and correlated with changes to one or more characteristic of a medium. As another example, the intensity may be measured for a plurality of wavelengths (e.g., at least two, at least five, at least ten, at least twenty, at least fifty, or more wavelengths) across a spectrum of light and changes to the intensity (or relative intensity) of the plurality of wavelengths may be correlated with at least one characteristic of the medium. Measurements can be performed at one or more discrete wavelengths or across a range of wavelengths. The one or more characteristics of the light can be measured, for example, using standard optical sensor analyzers (OSA).

The wavelength of light measured from the optical fiber may generally be any wavelength, for example, be from about 400 nm to about 2000 nm. Non-limiting examples of measured wavelengths include about 400 nm, about 500 nm, about 600 nm, about 700 nm, about 800 nm, about 900 nm, about 1000 nm, about 1100 nm, about 1200 nm, about 1300 nm, about 1400 nm, about 1500 nm, about 1600 nm, about 1700 nm, about 1800 nm, about 1900 nm, about 2000 nm, or a range between any two of these values.

In some embodiments, the light transmitted from the optical fiber may be combined with one or more other light sources before measuring one or more characteristics of the light. For example, the light transmitted through optical fiber may be superimposed with a reference light that is not transmitted through the optical fiber. The characteristic of the light (e.g., polarization) may be measured relative to the reference light (e.g., polarimetric interference).

In some embodiments, changes to the intensity of light transmitted through the optical fiber at one or more wavelengths can be correlated with one or more characteristics of the medium. Without being bound to any particular theory, the characteristics of the medium may be correlated, for example, with absorption of evanescent waves in the medium. The wavelength of light at which absorption occurs (or resonance) may be observed by changes to the intensity of light transmitted from the optical fiber. Meanwhile, changes to the intensity or wavelength of light absorbed by the medium may be correlated with changes to various characteristics of the medium, such as temperature, pressure, tension, index of refraction, or concentration of at least one component in the medium. The present application appreciates that including a slot within the optical fiber may increase the evanescent field, which may increase the sensitivity to changes in the medium.

In some embodiments, changes to the polarization of light transmitted through the optical fiber at one or more wavelengths can be correlated with one or more characteristics of the medium. Without being bound to any particular theory, the characteristic of the medium may be correlated, for example, with changes to the polarization of light transmitted through the optical fiber (e.g., birefringence). The polarity of the light may change, for example, due to the temperature, pressure, or strain in the medium, which alters the birefringence properties of the optical fiber. The present application appreciates that including a slot within the optical fiber may increase the birefringence properties of the optical fiber, which may increase sensitivity to changes in the medium.

The light that is transmitted through the optical fiber is not particularly limited and can be selected based upon the particular application. The light may include at least one wavelength of peak emission from about 400 nm to about 2000 nm. Non-limiting examples for the wavelength of peak emission include about 400 nm, about 500 nm, about 600 nm, about 700 nm, about 800 nm, about 900 nm, about 1000 nm, about 1100 nm, about 1200 nm, about 1300 nm, about 1400 nm, about 1500 nm, about 1600 nm, about 1700 nm, about 1800 nm, about 1900 nm, about 2000 nm, or a range between any two of these values. The light may be produced, for example, using commercially available light sources, such as a semiconductor light source or a broadband light source. The light may optionally be polarized or filtered before being transmitted through the optical fiber. In some embodiments, the at least one of the wavelengths measured are about the same as one of the wavelengths of peak emission for the light that is transmitted through the optical fiber.

Sensing Devices including Slotted Optical Fibers

Some embodiments disclosed herein include sensing devices having one or more slotted optical fibers. The slotted optical fiber can be any of the optical fibers disclosed in the present application. For example, any of the slotted optical fibers depicted in FIGS. 1-6 may be used. In some embodiments, the sensing device includes a light source, a slotted optical fiber, and a light detector. The optical fiber may be configured to receive at least a portion of the light from the light source at a first end and transmit the light to a second end of the optical fiber. The light detector may be configured to receive at least a portion of the light from the second end of the optical fiber and measure at least one characteristic of the light from the optical fiber.

Numerous light detectors are known in the art and are within the scope of the present application. For example, the light detector may be a standard optical spectrum analyzer (OSA). In some embodiments, the light detector is configured to measure at least one characteristic of the light selected from intensity, phase, and polarization. The light detector may be configured to measure one or more characteristics of light having a wavelength, for example, from about 400 nm to about 2000 nm. Non-limiting examples of wavelengths that the light detector may be configured to measure include about 400 nm, about 500 nm, about 600 nm, about 700 nm, about 800 nm, about 900 nm, about 1000 nm, about 1100 nm, about 1200 nm, about 1300 nm, about 1400 nm, about 1500 nm, about 1600 nm, about 1700 nm, about 1800 nm, about 1900 nm, about 2000 nm, or a range between any two of these values.

The light source is also not particularly limited and various commercially available light sources may be used. For example, the light source can be a semiconductor light source or a broadband light source. The light source may be configured to emit light having at least one wavelength of peak emission from about 400 nm to about 2000 nm. Non-limiting examples of wavelengths of peak emission that the light source may be configured to emit include about 400 nm, about 500 nm, about 600 nm, about 700 nm, about 800 nm, about 900 nm, about 1000 nm, about 1100 nm, about 1200 nm, about 1300 nm, about 1400 nm, about 1500 nm, about 1600 nm, about 1700 nm, about 1800 nm, about 1900 nm, about 2000 nm, or a range between any two of these values.

Various other optional components may be included in the device. For example, the device may include one or more polarizers for polarizing the light before or after transmitting through the optical fiber. The polarizer may be integrated with the light source. As another example, the device may include a splitter. The splitter may divide light from the light source before transmitting into the optical fiber. At least one beam of light from the splitter is not configured to transmit through the optical fiber. In some embodiments, at least two of the divided beams from the splitter are superimposed and received by the light detector (e.g., to measure polarimetric interference).

In some embodiments, the device also includes a processor coupled to the light detector and configured to receive signals from the light detector that correspond to at least one characteristic of the light from the optical fiber. The processor may also be configured to correlate at least one characteristic of the light from the optical fiber with at least one characteristic of a medium adjacent to or contacting the optical fiber. As an example, the processor may be coupled to machine-readable memory (e.g., flash memory, compact disk, magnetic disk, and the like) that includes data, such as a table, that correlates the intensity of light at a wavelength with the temperature of a medium. The processor may use this data with the signal received from the light detector to determine the temperature of the medium. The processor, in some embodiments, may also be coupled to the light source and configured to send and/or receive signals corresponding to at least on characteristic of the light from the light source. As an example, the processor may be configured to send or receives signals corresponding to the timing for emitting the light, the wavelength of light, or the intensity of the light emitted into the optical fiber. The processor may, for example, be integrated with the light detector and/or light source.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

EXAMPLES

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

Example 1

Simulation Procedures

The properties of the slotted optical fiber were simulated using full-vector finite-element analysis with COMSOL Multiphysics 3.4. The index of refraction for the optical fiber is the same as silica (1.444), while the medium surrounding the optical fiber is the same as air (1.000). The slotted microfiber was configured as depicted in FIG. 1C.

Example 2

Sensing using Birefringence of Slotted Optical Fiber

The $HE_{11}$ mode for two different polarizations was determined for a slotted optical fiber having a 1 µm diameter and a slot having a width of 150 nm and a depth of about 1 µm. The light transmitted through the optical fiber had a wavelength of 1550 nm. The non-degeneracy of the $HE_{11}$ mode is known as birefringence B of the slotted optical fiber. The birefringence B can be defined as $\beta=\eta_{eff}^{y}-\eta_{eff}^{x}$, where $\eta_{eff}^{y}$ and $\eta_{eff}^{x}$ are effective refractive indexes for $HE_{11}^{y}$ and $HE_{11}^{x}$. It was found that the corresponding electric field for the $HE_{11}^{x}$ mode exhibits a large discontinuity with increased amplitude within the slot due to the low index for air. Due to the large difference in index between air and silica, much of the field power is confined in the slot region. Meanwhile, the light wave polarization in the y-direction is satisfied because there is no flux between the slot and optical fiber. As such, the light is mostly confined in the higher index medium. Accordingly, much of the light polarized in the x-direction is transmitted through the air in the slot (e.g., the low index material), while very little light polarized in the y-direction is transmitted through the slot. It may be possible for about 10-20% of the optical power to be transmitted through the slot.

Figure 7:
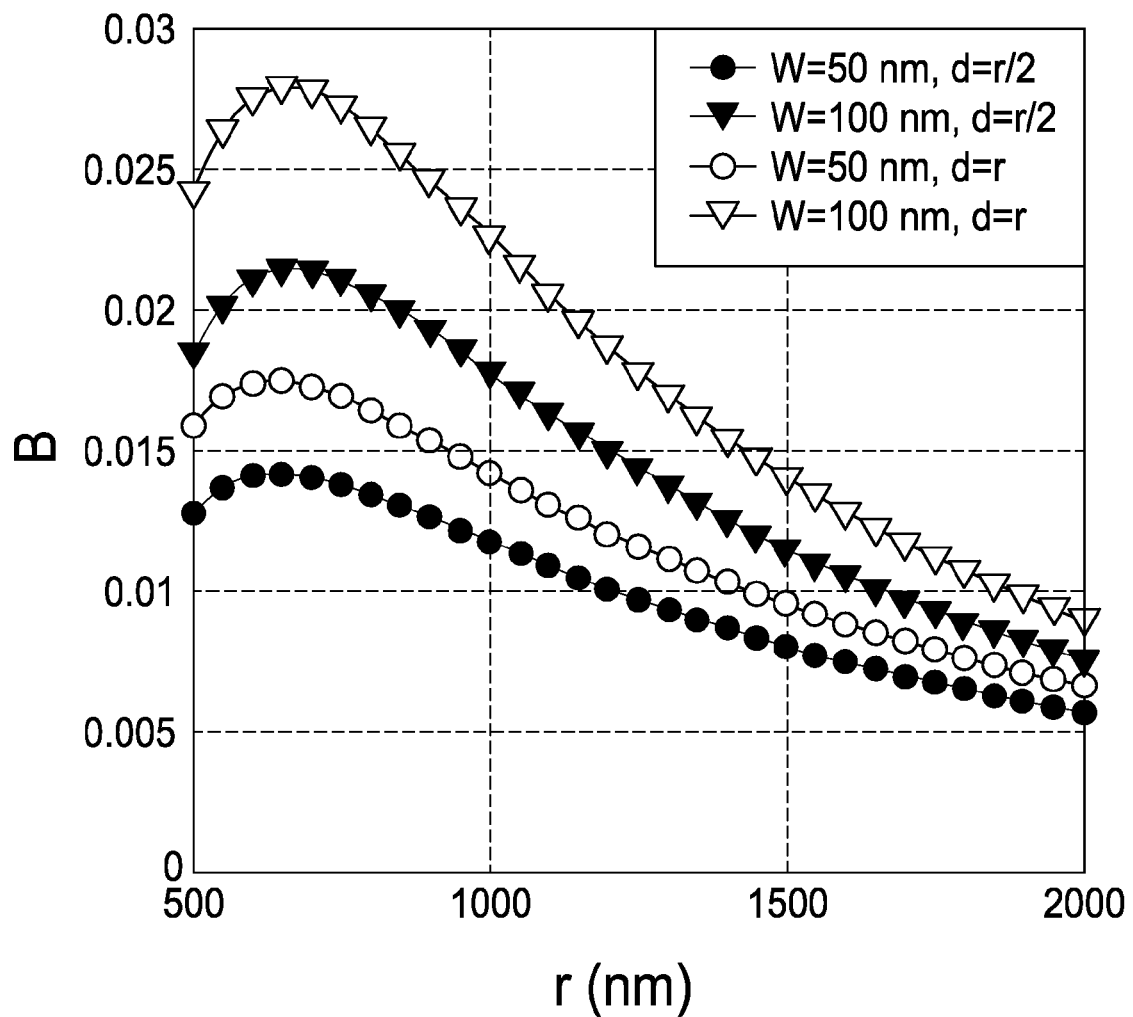
FIG. 7 is a graph showing the birefringence of various slotted optical fibers versus the radius of the optical fiber. The slot within the optical fiber was fixed at 50 nm or 100 nm, while the depth of the slot was either equal to or half of the radius of the optical fiber.

FIG. 7 is a graph showing the birefringence of various slotted optical fibers versus the radius of the optical fiber. The slot within the optical fiber was fixed at 50 nm or 100 nm, while the depth of the slot was either equal to or half of the radius of the optical fiber. This data demonstrates that the birefringence initially increases with the radius of the optical fiber to reach a maximum before decreasing. Also, the birefringence increases with the width and depth of the slot. These results demonstrate that the dimensions of the optical fiber can be selected to increase birefringence, which can increase sensitivity for various applications.

The sensitivity of the optical fiber can be considered as the change in the resonant wavelength relative to the change in the index of refraction:

$$S = \frac{\partial \lambda_0}{\partial \eta_{analyte}} = \frac{\partial \lambda_0}{\partial \beta} \frac{\partial \beta}{\partial \eta_{analyte}}.$$

Figure 8:
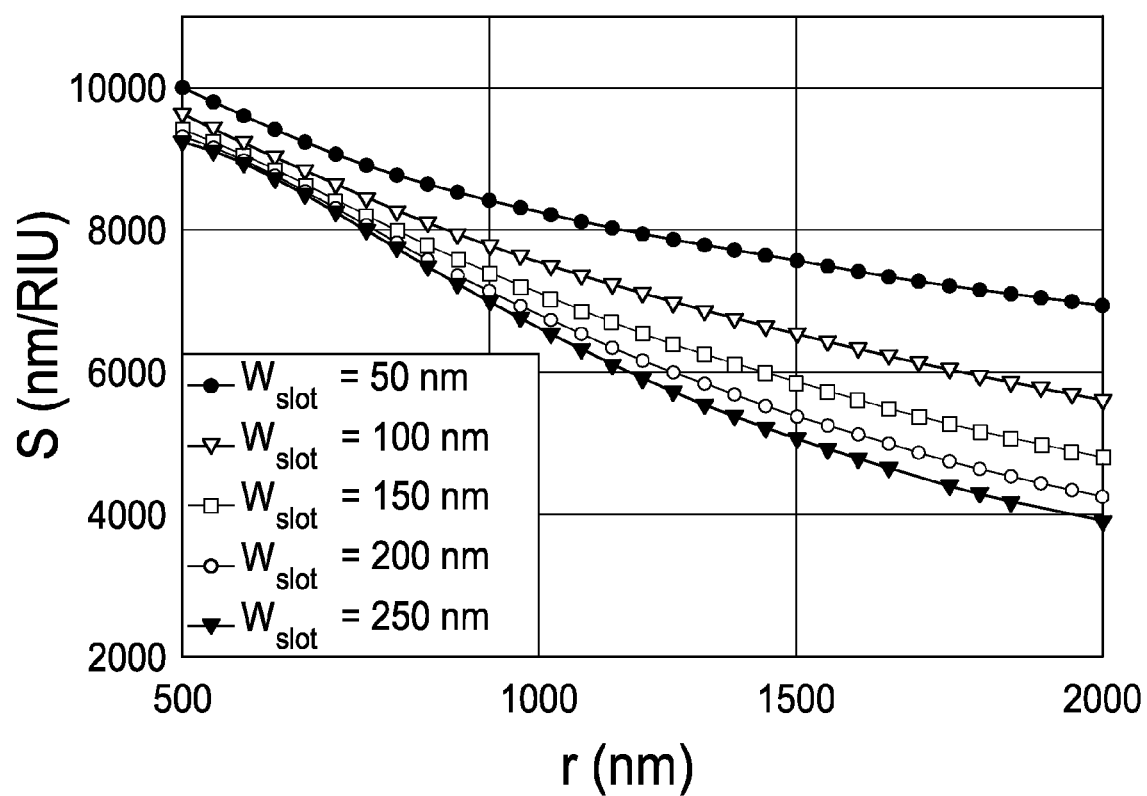
FIG. 8 is a graph showing the sensitivity for the optical fibers relative to the radius of the optical fiber. The depth of the slot in each fiber was about equal to the diameter of the optical fiber.

FIG. 8 is a graph showing the sensitivity for optical fibers relative to the radius of the optical fiber. The depth of the slot in each fiber was about equal to the diameter of the optical fiber. This data demonstrates that the slotted optical fiber can potentially achieve very high sensitivity to changes in the index of refraction in a surrounding medium.

Example 3

Evanescent Field Sensing using Slotted Optical Fiber

The evanescent field may be used to detect changes to the effective refractive index of a surrounding medium. The sensitivity can be obtained by monitoring the shift in the resonant frequency (e.g., the frequency or wavelength at which the medium absorbs light) of the medium:

$$S = \frac{\partial \lambda_0}{\partial \eta_{outside}} = \frac{\partial \lambda_0}{\partial \eta_{eff}} \frac{\partial \eta_{eff}}{\partial \eta_{outside}} \propto \frac{\partial \eta_{eff}}{\partial \eta_{outside}}.$$

Figure 9:
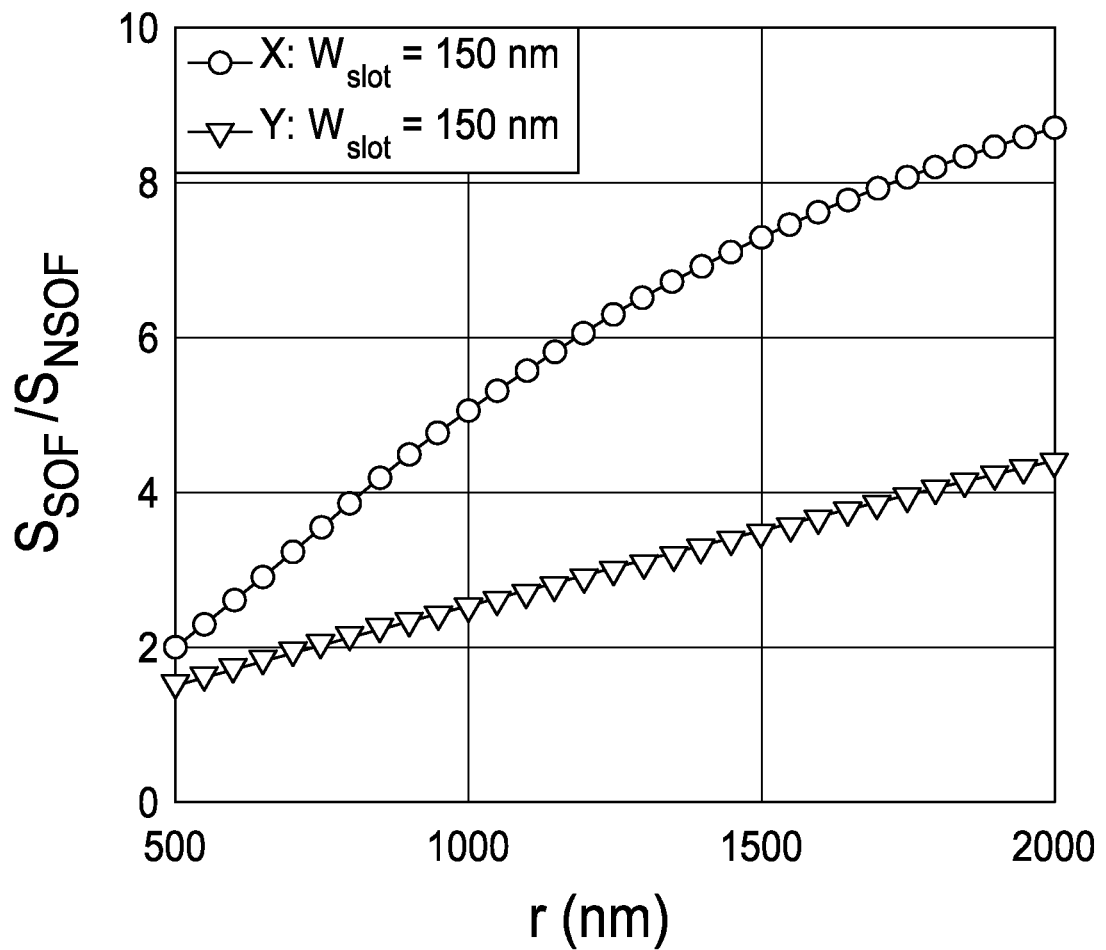
FIG. 9 is a graph showing the ratio of sensitivity for a slotted optical fiber relative (SOF) to a non-slotted optical fiber (NSOF) at varying radii for both the x- and y-polarization modes.

FIG. 9 is a graph showing the ratio of sensitivity for a slotted optical fiber (SOF) relative to a non-slotted optical fiber (NSOF) at varying radii for both the x- and y-polarization modes. These results indicate that the slotted optical fibers can exhibit between two and ten times the sensitivity compared to optical fibers without the slot. Accordingly, the slotted optical fiber may provide significantly improves sensitivity for sensing applications that use the evanescent field.

Example 4

Sensing Device

A slotted optical fiber having a 1 µm radius and 200 µm length is incorporated into a standard polarimetric interferometer. The optical fiber includes a slot as depicted in FIG. 1A-C, where the width is 150 nm, the depth is 1 and the length is 100 µm. A broadband light source is configured to emit light into a 3 dB coupler. The coupler is configured to divide the light into two beams of light: (i) a first beam that is received by a polarization controller, and (ii) a second beam of light that is superimposed with light transmitted through the optical fiber. The optical fiber is coupled at one end to a polarization controller that polarizes the light received by the optical fiber. The optical fiber is coupled at the second end with the coupler so that light transmitted through the optical fiber is superimposed with the second beam of light from the coupler as discussed above. An Optical Spectrum Analyzer (OSA) is configured to receive the superimposed light from the coupler. The analyzer is configured to measure the intensity, phase, and/or polarization of the received light over a range of wavelengths.

Accordingly, the optical fiber can be readily incorporated into conventional sensing devices.

Example 5

Temperature Sensing

The sensing device in Example can be used to detect changes in temperature. At least the slotted portion of the optical fiber contacts the ambient medium (e.g., air). The shift in interference wavelength detected by the analyzer may be correlated with the temperature of the ambient medium.

Example 6

Detecting Ethanol Content

The content of ethanol in an aqueous solution can be measured using the slotted optical fibers. The slotted optical fiber is used in a similar setup described in White, I. et al., "Refractometric Sensors for Lab-on-a-Chip Based on Optical Ring Resonators" *IEEE Sensors Journal*, vol. 7(1), pp. 28-35 (2007). Briefly, the light is emitted from a distributed feedback laser (about 1550 nm) that transmits through the slotted optical fiber and is received by a photodetector. The slotted optical fiber is coupled to a quartz conduit through evanescent coupling. A mixture of water and ethanol is feed through the conduit using a peristaltic pump. Shifts in the resonant wavelength of the light transmitted are detected and correlated with the amount of ethanol. The sensitivity (e.g., shift in resonant wavelength relative to the content of ethanol) may be increased by including the slotted optical fiber.

What is claimed is:

1. An optical fiber comprising: a first portion, a second portion, and at least one slot disposed between the first portion and the second portion, the slot extending along a longitudinal axis of the optical fiber,
wherein a cross-section of the optical fiber perpendicular to the longitudinal axis has a largest dimension less than or equal to about 4 μm, and the slot has a width of about 5 nm to about 500 nm and a depth of at least about 10 nm.

2. The optical fiber of claim 1, wherein the slot further comprises:
a first surface extending along the longitudinal axis of the optical fiber and adjacent to the , first portion of the optical fiber; and
a second surface extending along the longitudinal axis of the optical fiber and adjacent to the second portion of the optical fiber.

3. The optical fiber of claim 2, wherein the first surface is approximately planar and the second surface is approximately planar.

4. The optical fiber of claim 2, wherein the first surface extends from an outer surface of the optical fiber to an inner region of the optical fiber along an axis perpendicular to the longitudinal axis, and the second surface extends from an outer surface of the optical fiber to an inner region of the optical fiber along an axis perpendicular to the longitudinal axis.

5. The optical fiber of claim 2, wherein the first surface and the second surface are generally parallel.

6. The optical fiber of claims 2, wherein the slot further comprises a third surface extending between the first surface and the second surface.

7. The optical fiber of claim 6, wherein the third surface is generally planar.

8. The optical fiber of any one of claim 6 wherein the first surface and the third surface form a first angle of about 30° to about 150° and the second surface and third surface form a second angle of about 30° to about 150°.

9. The optical fiber of claim 2, wherein the first surface and the second surface meet to form a vertex, and wherein the first surface and a second surface form an angle of about 15° to about 120°.

10. The optical fiber of claim 9, wherein the vertex is located at about a center axis of the optical fiber.

11. The optical fiber of claim 1, wherein a center axis of optical microfiber is at least partially disposed within the slot.

12. The optical fiber of claim 1, wherein a length of the optical fiber is greater than a length of the slot.

13. The optical fiber of claim 1, wherein the optical fiber further comprises a third portion and a second slot disposed between the second portion and the third portion, wherein the second slot has a width of about 5 nm to about 500 nm and a depth of at least about 10 nm.

14. The optical fiber of claim 1, wherein the optical fiber has an attenuation coefficient at a wavelength of 1550 nm of about 2 dB/km or less.

15. The optical fiber of claim 1, wherein the optical fiber further comprises a plurality of gratings disposed on an outer surface of the optical fiber, wherein the gratings are spaced at repeating intervals along the longitudinal axis of the optical fiber.

16. A method for sensing characteristics of a medium, the method comprising:
providing an optical fiber disposed adjacent to a medium, wherein the optical fiber comprises: a first portion, a second portion, and at least one slot disposed between the first portion and the second portion, the slot extending along a longitudinal axis of the optical fiber, wherein a cross-section of the optical fiber perpendicular to the longitudinal axis has a largest dimension less than or equal to about 4 μm, and the slot has a width of about 5 nm to about 500 nm and a depth of at least about 10 nm;
transmitting light through the optical fiber from a first end of the optical fiber to a second end of the optical fiber; and
measuring at least one characteristic of the light from the optical fiber.

17. The method of claim 16, wherein the at least one characteristic of the light from the optical fiber is intensity, phase, or polarization.

18. The method of claim 16, further comprising correlating the at least one characteristic of the light from the optical fiber with at least one characteristic of the medium.

19. A sensing device comprising:
a light source;
an optical fiber configured to receive at least a portion of the light from the light source at a first end and transmit the light to a second end, wherein the optical fiber comprises: a first portion, a second portion, and at least one slot disposed between the first portion and the second portion, the slot extending along a longitudinal axis of the optical fiber, wherein a cross-section of the optical fiber perpendicular to the longitudinal axis has a largest dimension less than or equal to about 4 μm, and the slot has a width of about 5 nm to about 500 nm and a depth of at least about 10 nm; and
a light detector configured to receive at least a portion of the light from the second end of the optical fiber and measure at least one characteristic of the light from the optical fiber.

20. The sensing device of claim 19, wherein the at least one characteristic of the light from the optical fiber is intensity, phase, or polarization.

21. The sensing device of claim 19, the sensing device further comprising a processor coupled to the light detector and configured to receive signals corresponding to the at least one characteristic of the light from the optical fiber, and wherein the processor is further configured to correlate the at least one characteristic of the light from the optical fiber with at least one characteristic of a medium adjacent to the optical fiber.

* * * * *

UNITED STATES PATENT AND TRADEMARK OFFICE
CERTIFICATE OF CORRECTION

Page 1 of 2

PATENT NO. : 8,644,652 B2
APPLICATION NO. : 13/510925
DATED : February 4, 2014
INVENTOR(S) : Xu et al.

It is certified that error appears in the above-identified patent and that said Letters Patent is hereby corrected as shown below:

On the Title Page, in Item (56), under "OTHER PUBLICATIONS", in Column 2, Line 7, delete "Phonics," and insert -- Photonics, --, therefor.

In The Specification

In Column 2, Line 35, delete "thereof" and insert -- thereof. --, therefor.

In Column 3, Line 51, delete "shows a" and insert -- show a --, therefor.

In Column 4, Line 11, delete "relative (SOF)" and insert -- (SOF) relative --, therefor.

In Column 5, Line 2, delete "first vertex 180" and insert -- first vertex 170 --, therefor.

In Column 7, Line 57, delete "first vertex 180" and insert -- first vertex 170 --, therefor.

In Column 9, Line 50, delete "250" and insert -- 250 μm; --, therefor.

In Column 10, Line 13, delete "slot 100" and insert -- slot 110 --, therefor.

In Column 11, Lines 1-2, delete "Third slot 620" and insert -- Third slot 630 --, therefor.

In Column 11, Line 3, delete "Fourth slot 620" and insert -- Fourth slot 640 --, therefor.

In Column 11, Line 4, delete "fourth portion 670" and insert -- fourth portion 680 --, therefor.

In Column 18, Line 22, delete "1 and" and insert -- 1 μm, and --, therefor.

Signed and Sealed this
Ninth Day of December, 2014

Michelle K. Lee
*Deputy Director of the United States Patent and Trademark Office*

CERTIFICATE OF CORRECTION (continued)
U.S. Pat. No. 8,644,652 B2

In The Claims

In Column 19, Line 15, in Claim 2, delete "the , first" and insert -- the first --, therefor.

In Column 19, Line 32, in Claim 6, delete "claims" and insert -- claim --, therefor.

In Column 19, Line 37, in Claim 8, delete "of any one of claim" and insert -- of claim --, therefor.